(12) United States Patent
Streff

(10) Patent No.: US 8,851,890 B2
(45) Date of Patent: Oct. 7, 2014

(54) IMPRESSION CAP FOR A DENTAL IMPLANT

(75) Inventor: Patrick Streff, Basel (CH)

(73) Assignee: Straumann Holding AG, Basel (CH)

( * ) Notice: Subject to any disclaimer, the term of this patent is extended or adjusted under 35 U.S.C. 154(b) by 221 days.

(21) Appl. No.: 13/069,880

(22) Filed: Mar. 23, 2011

(65) Prior Publication Data

US 2011/0236854 A1    Sep. 29, 2011

(30) Foreign Application Priority Data

Mar. 25, 2010    (EP) .................................... 10003184

(51) Int. Cl.
*A61C 8/00*    (2006.01)

(52) U.S. Cl.
CPC .................................... *A61C 8/0001* (2013.01)
USPC .......................................................... 433/173

(58) Field of Classification Search
USPC ........................ 433/172–176, 201.1, 213–214
See application file for complete search history.

(56) References Cited

U.S. PATENT DOCUMENTS

| | | | |
|---|---|---|---|
| 5,213,502 A | 5/1993 | Daftary | |
| 5,733,122 A * | 3/1998 | Gordon | 433/172 |
| 6,045,361 A | 4/2000 | Misch et al. | |
| 6,068,478 A * | 5/2000 | Grande et al. | 433/172 |
| 6,213,773 B1 | 4/2001 | Gittleman | |
| 6,332,777 B1 * | 12/2001 | Sutter | 433/173 |
| 6,379,148 B1 | 4/2002 | Chen | |
| 6,382,977 B1 | 5/2002 | Kumar et al. | |
| 6,508,650 B2 | 1/2003 | Gittleman | |
| 6,524,106 B1 | 2/2003 | Ziegler | |
| 7,066,736 B2 | 6/2006 | Kumar et al. | |
| 2003/0104336 A1 * | 6/2003 | Sethi et al. | 433/141 |
| 2003/0170587 A1 | 9/2003 | Augthun et al. | |
| 2003/0170588 A1 | 9/2003 | Augthun et al. | |
| 2004/0096804 A1 | 5/2004 | Vogt et al. | |
| 2006/0121416 A1 * | 6/2006 | Engman | 433/173 |

FOREIGN PATENT DOCUMENTS

| | | |
|---|---|---|
| EP | 0 747 017 A2 | 11/1996 |
| EP | 1 252 866 A1 | 4/2001 |
| EP | 1 985 256 A1 | 2/2006 |
| EP | 1 274 366 B1 | 11/2007 |
| EP | 1 274 365 B1 | 6/2008 |
| WO | WO 97/28755 A1 | 8/1997 |
| WO | WO 98/52490 A1 | 11/1998 |

(Continued)

OTHER PUBLICATIONS

European Search Report and Written Opinion in EP 10003184.8 dated Aug. 4, 2010.

(Continued)

*Primary Examiner* — Yogesh Patel
(74) *Attorney, Agent, or Firm* — Novak Druce Connolly Bove + Quigg LLP

(57) ABSTRACT

Impression cap for a dental implant, with a recess (8) extending in the longitudinal direction between two end areas (4, 6) of the impression cap. The recess is configured in such a way that it can receive a fastening element, which is intended to connect the impression cap to the dental implant via a first of the two end areas (4). The impression cap, at its second end area (6) remote from the first end area, has a connection element that is configured in such a way as to produce a releasable snap-fit connection between the impression cap and the dental implant.

14 Claims, 4 Drawing Sheets

(56) References Cited

FOREIGN PATENT DOCUMENTS

| WO | WO 00/02497 A1 | 1/2000 |
| WO | WO 02/17814 A1 | 3/2002 |
| WO | WO 03/003933 A1 | 1/2003 |
| WO | WO 2004/039280 A1 | 5/2004 |
| WO | WO 2007/093648 A1 | 8/2007 |
| WO | WO 2009/024838 A2 | 2/2009 |

OTHER PUBLICATIONS

Schroeder, A. et al., "Orale Implantologie" [Oral Implantology] 2$^{nd}$ edition, Georg Thieme Verlag Strettgart, 1994, pp. 202 et seq. (English Translation, The Concept of the ITI Implants, pp. 198-204).

* cited by examiner

IMPRESSION CAP FOR A DENTAL IMPLANT

FIELD OF THE INVENTION

The present invention relates to an impression cap for a dental implant, and to the use of the impression cap for taking an open-tray and/or closed-tray impression of a reference implant.

BACKGROUND

In the field of oral implantology, the exact positioning of the dental implant in the jaw bone of the patient is crucial to the success of the treatment. This is especially so when the amount of available bone for anchoring the dental implant is limited.

The problem of exact positioning can be addressed, for example, by using a drilling jig in which the at least one opening serves as a drill guide and exactly predetermines the position of the respective dental implant and of the hole drilled for the latter. A suitable technique is described in WO 03/003933, for example, which relates to the production of a super-structure provided with tooth prostheses. Specifically, the method in question comprises the steps of fixing a reference element (hereinafter also called "reference implant") in the jaw bone, then taking an impression of the jaw bone with the reference element fixed therein. A temporary model of the superstructure is then prepared on the basis of the impression. The model is then placed onto the reference elements, after which a computed tomogram of the jaw and of the model is prepared. The information obtained from the computed tomogram concerning the anatomical structures in the jaw, for example the position of nerve strands and blood vessels, in spatial relationship to the superstructure, allows a suitable choice to be made as regards the position of the holes drilled for the implants. On the basis of the chosen positions, a drilling jig is then prepared which has means for fixing to the reference elements and in which the openings exactly predetermine the position of the respective drilled hole.

A step that is of critical importance involves taking the impression of the jaw with the reference elements, which impression serves as a basis for the preparation, first, of the temporary model and, second, of the drilling jig.

Methods of taking impressions for dental implants have been described many times in the prior art, for example in Schroeder, A. et al., "Orale Implantologie" [Oral implantology], $2^{nd}$ edition, Georg Thieme Verlag Stuttgart, 1994, page 202 et seq. Reference is also made, by way of example, to EP-A-1274365, EP-A-1274366, WO2007/093648, U.S. Pat. No. 6,213,773, U.S. Pat. No. 6,379,148, U.S. Pat. No. 6,524,106, U.S. Pat. No. 6,508,650, EP-A-0747017 and U.S. Pat. No. 6,045,361. Basically analogous methods are available for taking impressions of reference elements anchored in the jaw bone.

In the customary methods, the impression is generally taken using an impression coping, which usually has an impression cap and, connected to the latter, a suitable fastening element for fastening the impression cap to the dental implant. Using an impression tray, the space around the impression coping and the adjacent tissue structures in the patient's mouth is filled with an initially plastically deformable impression compound that can harden. The impression compound, after hardening, is removed from the patient's mouth and forms a negative model, on the basis of which the temporary model can be prepared.

In the customary methods of taking impressions, a distinction is made between what are called open-tray impressions and closed-tray impressions. The two methods of taking impressions are described, for example, in U.S. Pat. No. 7,066,736.

When taking open-tray impressions, the connection established, by means of the fastening element, between the impression cap and the dental implant is actively undone before the impression compound is removed from the patient's mouth. Since the fastening element is generally in the form of a screw, the impression tray has, in a corresponding area, an aperture through which the screw can be gripped, for example using a screwdriver, and the screw connection can thus be actively undone.

When the impression tray is removed, the impression cap remains in the impression compound in the open tray technique. This means that the position of the dental implants, in respect of the spatial situation in the patient's mouth, can be transferred exactly to the negative model. Impression copings that can be used for taking open-tray impressions are described, for example, in U.S. Pat. No. 5,213,502 and in US-A-2006/0121416.

By contrast, when taking closed-tray impressions, the connection between impression cap and dental implant is not actively undone before removal of the impression compound, with the result that a corresponding opening does not have to be provided in the impression tray. It is conceivable for the impression cap to remain on the dental implant, as is described in WO 2004/039280, for example. In this case, the impression cap is generally inserted again in a further step into the hardened impression compound, i.e. into the negative model. This can lead to inaccuracies, especially if the necessary care is not taken when reinserting the impression cap into the negative model. Alternatively, the impression cap can be designed in such a way that the connection between impression cap and dental implant is undone during removal. A corresponding impression cap is disclosed in U.S. Pat. No. 6,382,977, for example.

An open-tray or a closed-tray impression may be indicated depending on the situation presented in the patient's mouth. Accordingly, different impression caps are used depending on the chosen type of impression.

Against this background, WO 00/02497 and WO 2004/039280 are concerned, for example, with the problem of making available an impression system which can be used both for the open-tray technique and also the closed-tray technique. However, according to the systems described in these documents, the impression cap in the open-tray technique remains on the dental implant and not in the impression compound removed from the jaw, and this can give rise to the above-described problems concerning the accuracy of the transfer.

SUMMARY OF THE INVENTION

In accordance with one embodiment of the present invention, an impression cap is provided for dental implants, in particular for reference implants, that ensures an exact transfer of the position of the dental implants both in the closed-tray technique and also in the open-tray technique.

According to the present invention, the impression cap has a recess extending in the longitudinal direction between two end areas of the impression cap and is therefore substantially sleeve-shaped. The recess is configured in such a way that it can receive a fastening element, which is intended to connect the impression cap to the dental implant via a first of the two end areas.

According to one embodiment of the invention, the second end area remote from the first end area comprises a connection element, which is configured in such a way as to produce a releasable snap-fit connection between the impression cap and the dental implant.

According to one embodiment of the invention, the impression cap thus has a first end area, via which the impression cap can be connected to the dental implant for an open-tray impression, and a second end area, via which the impression cap can be connected to the dental implant for a closed-tray impression.

According to one embodiment of the invention, both end areas are configured to be connected directly to the dental implant.

By virtue of the configuration, according to one embodiment of the invention, of the connection element for the closed-tray impression, the connection is undone when a predetermined tensile force is exceeded. In this way, in the closed-tray technique too, the connection between dental implant and impression cap is undone by the tensile force acting on the impression cap upon removal of the impression compound, and the impression cap thus remains in the impression compound. The present invention thus permits very exact transfer of the position of the dental implant in both the open and closed tray methods of taking impressions.

According to a preferred embodiment, the connection element is in the form of an elastically deformable snap-fit lip, which is generally formed on the periphery of the impression cap and on the second end area thereof. The snap-fit lip is preferably configured in such a way as to engage behind a snap-fit edge on the outside of the dental implant. The snap-fit lip preferably has a radially encircling configuration.

When connecting the impression cap to the dental implant for the closed-tray technique, the snap-fit lip is elastically widened until it can be pushed over the snap-fit edge and can engage behind the latter. The connection is undone by the snap-fit lip being pushed in the opposite direction over the snap-fit edge, as is the case in the closed-tray technique when the impression compound, with the impression cap embedded therein, is removed from the jaw.

As an alternative to the described snap-fit lip, it is also conceivable that the connection element has elastically deformable fingers that are intended to engage in a corresponding opening of the dental implant and to engage behind an internal snap-fit edge. It is also conceivable that the connection element has a spring, by means of which the snap-fit connection is produced.

As an alternative to the closed-tray technique of taking impressions that has been described, the open-tray technique is likewise possible according to the invention and is performed by means of an additional fastening element. In general, the impression cap has a contact surface designed in such a way as to cooperate with a preferably correspondingly configured mating contact surface of the fastening element. This makes it possible to ensure a firm connection between impression cap and dental implant when taking the impression. The fastening element is generally in the form of a screw that engages at least partially through the recess in the impression cap. This screw generally has a head part and a shank part with an externally threaded portion, the external thread of the screw corresponding to an internal thread formed generally in the coronal opening of the dental implant. In this embodiment, the contact surface is generally formed by the head part of the screw.

Generally, the recess is substantially cylindrical at least in some sections. In particular, it is conceivable for a constriction to be formed in the recess, said constriction forming a shoulder surface that protrudes radially into the interior of the recess and that serves as a contact surface for the fastening element.

The shoulder surface of the constriction, protruding radially into the interior of the recess, is preferably conical. According to this embodiment, it is possible to ensure the least possible play between fastening element and dental implant, which is important for taking a very accurate impression. Moreover, in this embodiment, the force acting on the impression cap is distributed over a large surface area.

If, as has been described above, the fastening element is in the form of a screw, the constriction can additionally ensure effective protection against uncoupling of impression cap and screw. This is the case, for example, when in addition to the external diameter of the head part of the screw, the external diameter of the externally threaded portion is greater than the internal diameter of the constriction.

As regards the open-tray impression technique, the impression cap according to the invention has the further advantage that the connection element of the second end area, standing free in the described impression technique, can be used as a docking site for an attachment part. For example, such an attachment part can be intended to close the recess at its free end too, by means of which it is possible to avoid penetration of the impression compound into the recess while the impression is being taken.

Both end areas of the impression cap generally have a bearing surface configured in such a way as to bear on a mating contact surface of matching configuration on the dental implant. This avoids a situation where, in the assembled state, hollow spaces are present into which the impression compound could penetrate while the impression is being taken.

Since the bearing surface of the dental implant, and in particular of the reference implant for which the present invention is primarily intended, generally has a conical shoulder surface as the mating bearing surface, the corresponding bearing surface of the impression cap is preferably likewise at least partially conical.

In order to ensure the closest possible form fit between the impression cap and the hardened impression compound, the impression cap preferably has a profile on the outside. The profile can be provided, for example, in the form of radial depressions or protuberances.

As has been mentioned at the outset, the impression cap is suitable in particular for the open-tray and/or closed-tray technique of taking impressions of reference implants, as are used, for example, for the preparation of drilling jigs. In principle, however, it is also conceivable for it to be used for any other dental implant.

If the impression cap according to one embodiment of the invention is used for taking impressions of temporarily fitted reference implants, it is generally possible to dispense with the anti-twist safety feature between impression cap and dental implant, which is in most cases necessary for permanently fitted conventional dental implants. It is thus possible to avoid the static friction between impression cap and dental implant, which is caused by this anti-twist safety feature, and also the associated inaccuracy upon transfer to the negative model, which is caused by plastic deformation of the impression compound. Alternatively, however, an anti-twist safety feature can also be provided if so desired for the particular purposes. Accordingly, at least one of the two end areas of the impression cap can have a polygonal base or a polygonal opening, which base or opening is designed to exactly fit the opening or base in the coronal end area of the dental implant.

BRIEF DESCRIPTION OF THE DRAWINGS

The invention is described in more detail with reference to the attached figures, in which.

DETAILED DESCRIPTION

Figure 1:
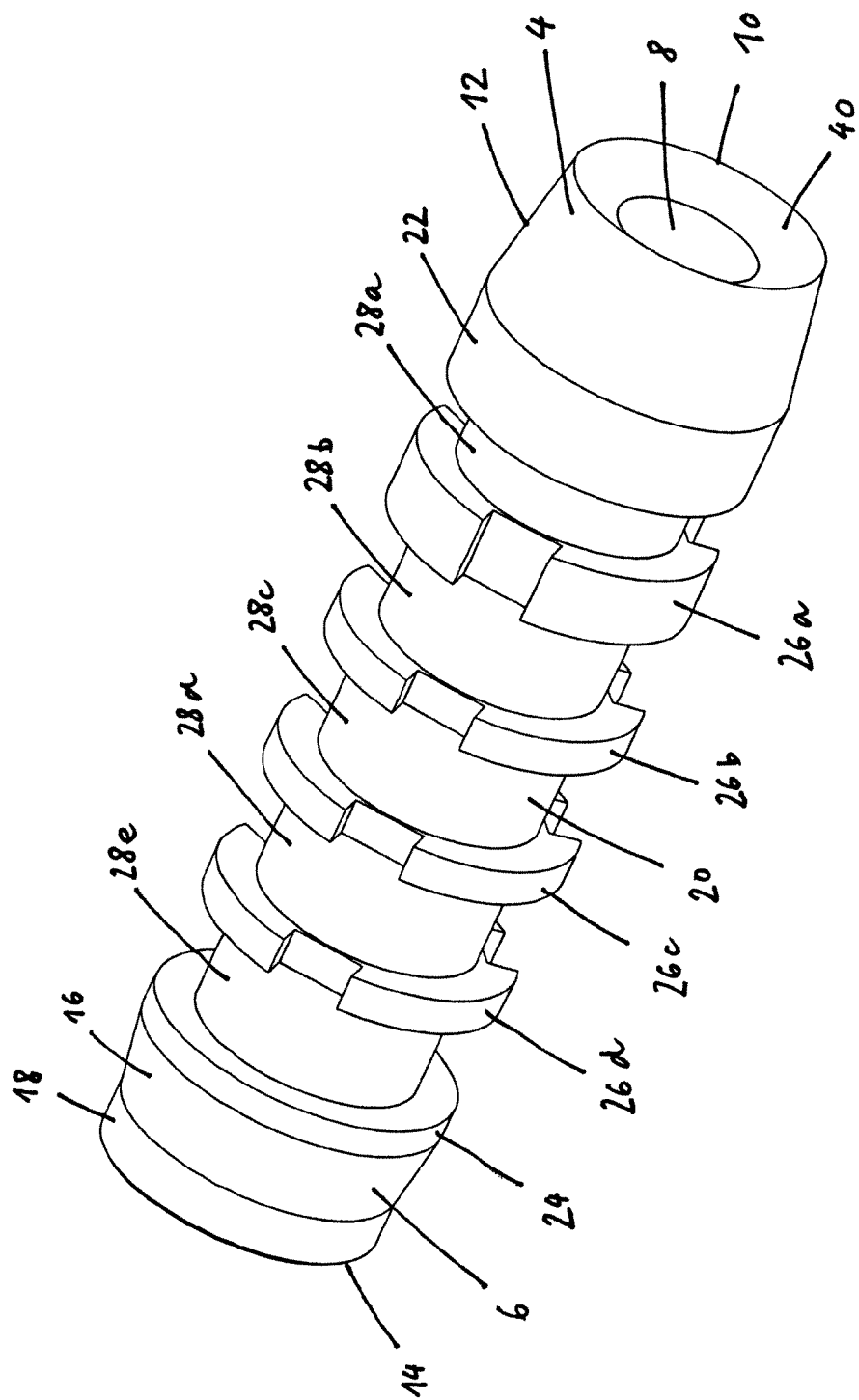
FIG. 1 shows a perspective view of an impression cap according to one embodiment of the invention.
Figure 2:
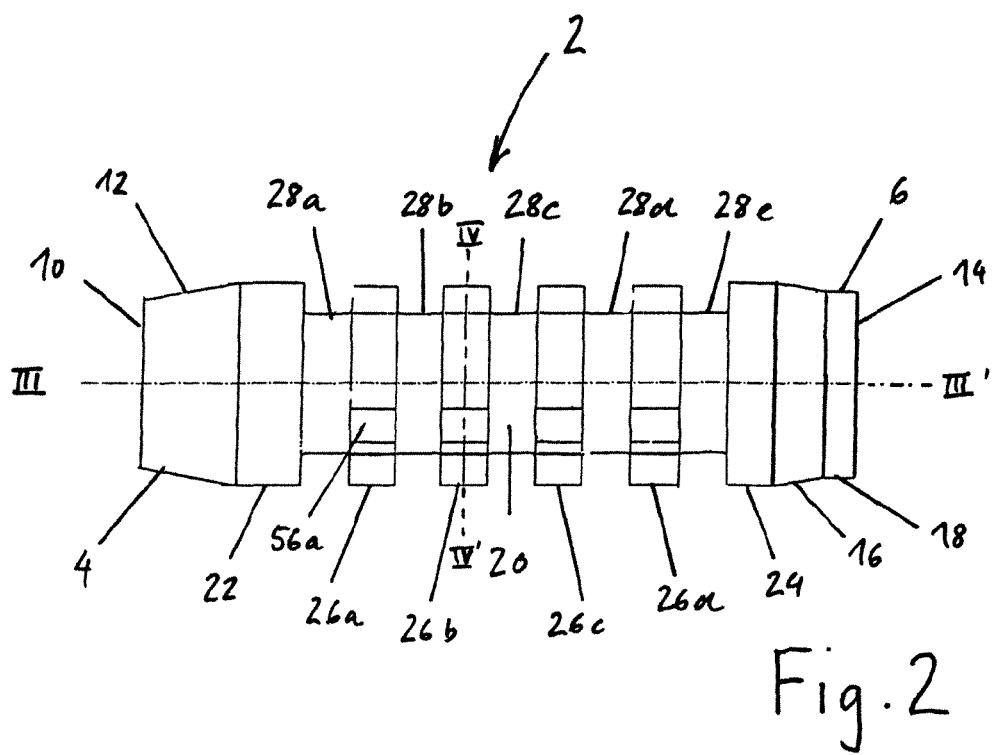
FIG. 2 shows a side view of another impression cap according to one embodiment of the invention.

As is shown in FIGS. 1 and 2, the impression cap 2 according to one embodiment of the present invention has a first end area 4 and a second end area 6. A recess 8 extends in the longitudinal direction between the end areas.

As can be seen in particular from FIG. 2, the first end area 4 is shaped in profile as a cone 12 tapering in the direction of the first end 10, the cone angle being approximately 10° in the view illustrated. The second end area 6 is shaped in profile as a cone 16 tapering in the direction of the second end 14, which cone 16 is adjoined by a circular cylindrical area 18. The cone angle of said cone 16 is likewise approximately 10° in the view illustrated.

Between the first end area 4 and the second end area 6 there is a middle area 20, with circular cylindrical edge segments 22 and 24 adjoining the end areas 4 and 6, respectively, and with four profiling segments 26a, 26b, 26c and 26d, which lie between the edge segments, spaced uniformly apart in the longitudinal direction and separated from one another and from the edge segments 22 and 24 by radial depressions 28a, 28b, 28c, 28d and 28e. The impression cap in FIG. 1 differs from the one in FIG. 2 mainly in that the profiling segment 26a directed toward the first end 10 is wider in the longitudinal direction than the other profiling segments 26b, 26c, 26d. In the embodiment shown in FIG. 2, all of the profiling segments are basically of identical shape.

Figure 3:
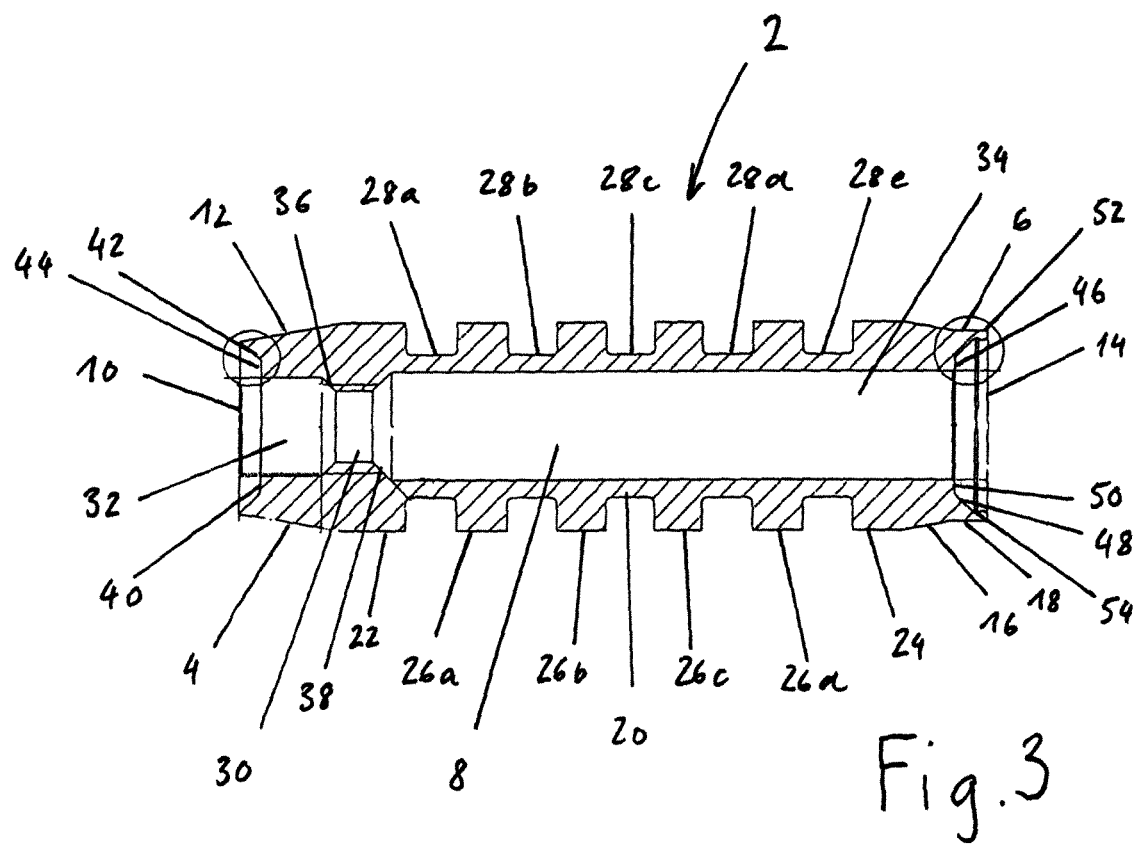
FIG. 3 shows the impression cap according to FIG. 2 in longitudinal section along line III-III'.

As can be seen in particular from FIG. 3, a constriction 30 formed in the recess 8 is arranged between a first recess portion 32 extending toward the first end 10 and a second recess portion 34 extending toward the second end 14. Said recess portions 32, 34 are substantially of circular cylindrical shape and taper conically toward the likewise circular cylindrical constriction 30. The conical shoulder surfaces 36, 38 thus formed have a cone angle of approximately 45° in the view illustrated.

The first end area 4 has, on the inside, a bearing surface 40 which, in the direction from the first end 10, comprises a first, conically extending surface portion 42 and, adjoining the latter, a second surface portion 44 extending at right angles to the longitudinal direction of the impression cap 2.

Analogously, the second end area 6 also has, on the inside, a bearing surface 46 which, in the direction from the second end 14, comprises a first, conically extending surface portion 48, and a second surface portion 50 extending at right angles to the longitudinal direction of the impression cap 2. A radially encircling snap-fit lip 52 is integrally formed peripherally on the bearing surface 46 of the second end area 6 and has, in cross section, the shape of an inwardly protruding bead. At the boundary between the snap-fit lip 52 and the bearing surface 46, an inner edge 54 is formed whose internal diameter corresponds substantially to the external diameter of the snap-fit edge of the dental implant.

Figure 4:
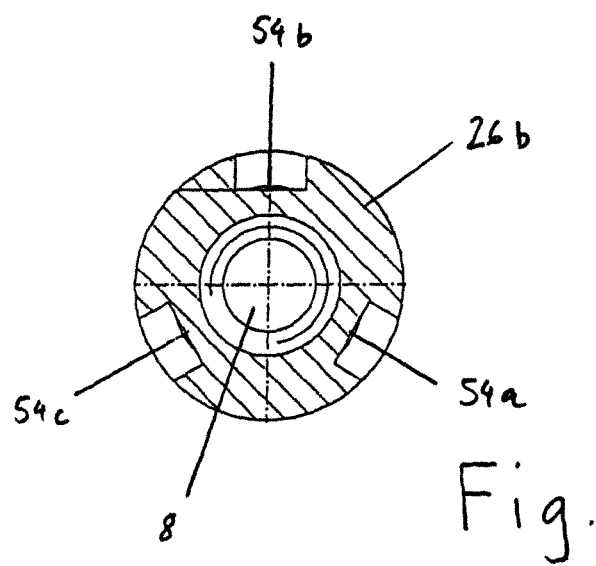
FIG. 4 shows the impression cap according to FIG. 2 in cross section along line IV-IV'.

As can be seen in particular from FIG. 4, the profiling segments 26a, 26b, 26c and 26d in the embodiment shown have three depressions 56a, 56b and 56c, which extend in the longitudinal direction and which are arranged uniformly in the circumferential direction and are thus spaced apart from one another by ca. 120°.

The impression cap shown can be used for taking both open-tray impressions and also closed-tray impressions. When taking open-tray impressions, the impression cap 2 is connected to a dental implant (not shown) via the first end area 4, by means of a fastening element (not shown) engaging at least partially through the recess 8. The bearing surface 40 of the first end area thus generally bears on a mating bearing surface of matching shape on the dental implant. The fastening element is generally in the form of a screw, which comprises a shank part with an externally threaded portion and a head part with a notch for a screwdriver. In its area adjoining the shank part, the head part is generally conical and thus forms a mating contact surface of a shape matching the contact surface formed by the conical inner surfaces 38 of the impression cap 2. This allows the impression cap 2 to be fastened to the dental implant with the least possible play, and the force acting on the impression cap is distributed over a large surface area.

When taking impressions, the impression compound penetrates into the radial depressions 28a-e between the profiling segments 26a-d and into the depressions 56a-c of the profiling segments 26a-d, thus ensuring the closest possible form fit between the impression compound and the impression cap. The profiling can be differently configured depending on the result to be achieved. For example, it is conceivable in particular for the radial depressions 28a-e shown in the figures to be made wider, with a correspondingly narrower configuration of the profiling segments 26a-d. A wider configuration of the depressions means that the impression compound, even when it has a relatively high viscosity, can penetrate into the depressions and thereby ensure an optimal form fit after it hardens.

After the impression has been taken, the screw connection is undone by unscrewing the screw through the recess 8, for example by means of a screw driver.

Alternatively, when taking a closed-tray impression, the impression cap 2 is placed onto the dental implant by means of the snap-fit lip 52 being widened so far that it can be pushed over a snap-fit edge of the dental implant. After the impression compound has hardened, the impression compound, with the impression cap 2 embedded therein, is lifted away from the dental implant. In doing so, the snap-fit lip 52 is again widened and pushed over the snap-fit edge, as a result of which the snap-fit connection is canceled. The impression cap 2 thus remains in the hardened impression compound.

The invention claimed is:

1. An impression cap configured for a dental implant, the impression cap comprising:

a recess extending in a longitudinal direction between a first end area and a second end area of the impression cap, wherein both end areas are configured to be connected directly to a dental implant, the recess is configured to receive a fastening element to connect the impression cap to a dental implant via a first end area, the first end area having an internal shoulder for mating with the fastening element, wherein the impression cap, at the second end area remote from the first end area, has a connection element configured to produce a releasable snap-fit connection between the impression cap and a dental implant, the connection element comprising an elastically deformable snap-fit lip; the second end area having a cone profile, wherein the second cone profile is adjoined by a circular cylindrical end portion and the first end area having a conical profile;

wherein the first end area is configured to be connected to a dental implant for an open-tray impression and the second end area is configured to be connected to a dental implant for a closed-tray impression.

2. The impression cap as claimed in claim 1, wherein the second end area has an inner edge of an internal diameter for mating with an external diameter of a dental implant.

3. The impression cap as claimed in claim 2, wherein the snap-fit lip is configured to engage behind a snap-fit edge on an outside surface of a dental implant.

4. The impression cap as claimed in claim 2, wherein the snap-fit lip has a radially encircling configuration.

5. The impression cap as claimed in claim 1, the first end area having a contact surface configured to cooperate with a mating contact surface of a fastening element.

6. The impression cap as claimed in claim 5, wherein the contact surface is formed by a conical shoulder surface protruding radially into the interior of the recess.

7. The impression cap as claimed in claim 1, wherein both end areas have a bearing surface configured to bear on a mating contact surface of a matching configuration on a dental implant.

8. The impression cap as claimed in claim 7, wherein the bearing surface is formed on an inside surface of the cap.

9. The impression cap as claimed in claim 1, wherein the impression cap has a profiling on an outside surface thereof.

10. The impression cap as claimed in claim 1, wherein at least one of the two end areas has an at least partially conical bearing surface configured to bear on a mating bearing surface of a matching shape on a dental implant.

11. The impression cap as claimed in claim 1, further comprising a fastening element engaging at least partially through the recess.

12. The impression cap as claimed in claim 11, wherein the fastening element is a screw.

13. A method of using the impression cap as claimed in claim 1, comprising taking an impression of a reference implant.

14. A method of using the impression cap as claimed in claim 1, comprising taking an open-tray and/or closed-tray impression of a reference implant.

* * * * *